United States Patent

Morisawa et al.

[11] 4,094,982
[45] June 13, 1978

[54] PYRIDINE SULFONAMIDES AND THEIR USE AS ANTICOCCIDIAL AGENTS

[75] Inventors: Yasuhiro Morisawa; Mitsuru Kataoka; Noritoshi Kitano; Toshiaki Mastuzawa, all of Tokyo, Japan

[73] Assignee: Sankyo Company Limited, Tokyo, Japan

[21] Appl. No.: 681,154

[22] Filed: Apr. 28, 1976

[30] Foreign Application Priority Data

May 15, 1975 Japan .................... 50-58180
Dec. 9, 1975 Japan .................... 50-146501

[51] Int. Cl.$^2$ .................... C07D 213/02; A01N 9/22
[52] U.S. Cl. .................... 424/263; 260/294.8 F
[58] Field of Search .................... 260/294.8 F; 424/263

[56] References Cited

U.S. PATENT DOCUMENTS

2,170,209  8/1939  Naegeli .................... 260/294.8 F

OTHER PUBLICATIONS

Graboyes et al., J. Am. Chem. Sec., vol. 79, (24), pp. 6421–6426, Dec. 20, 1957.
Rogers et al., Chem. Abstracts, vol. 63, (10), p. 14,641-f, Nov. 8, 1965.
Burger, Medicinal Chemistry, Third Edition, Part 1, Wiley-Interscience, pp. 570–572, 1970.

*Primary Examiner*—Alan L. Rotman
*Attorney, Agent, or Firm*—Flynn & Frishauf

[57] ABSTRACT

Pyridine derivatives having the formula

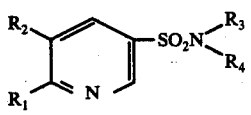
(I)

wherein
$R_1$ represents hydrogen atom, amino group or a group

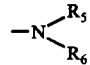

in which $R_5$ and $R_6$ may be the same or different and each represents an alkyl group of 1 to 4 carbon atoms or $R_5$ is hydrogen atom and $R_6$ represents an alkyl group of 1 to 4 carbon atoms, an alkenyl group of 3 or 4 carbon atoms or a benzyl group optionally substituted with halogen, cyano, alkyl of 1 to 4 carbon atoms or alkoxy of 1 to 4 carbon atoms;

$R_2$ represents nitro group, amino group or an alkylamino group of 1 to 3 carbon atoms;

$R_3$ and $R_4$ individually represent hydrogen atom, an alkyl group of 1 to 4 carbon atoms, an alkoxyalkyl group which has 1 to 4 carbon atoms in the alkoxy moiety and 2 to 4 carbon atoms in the alkyl moiety, an alkenyl group of 3 or 4 carbon atoms, an alkanoyl group of 1 to 18 carbon atoms or a benzyl group optionally substituted with halogen, cyano, alkyl of 1 to 4 carbon atoms or alkoxy of 1 to 4 carbon atoms; provided that when $R_1$ is hydrogen atom and $R_2$ is nitro group, $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group, said alkenyl group, said alkanoyl group or said benzyl group, when $R_1$ is hydrogen atom and $R_2$ is amino group or said alkylamino group, $R_3$ and $R_4$ individually is hydrogen atom or they may be the same or different and each represents said alkyl group, when $R_1$ is amino group and $R_2$ is nitro group, $R_3$ and $R_4$ may be the same or different and each represents said alkyl group or $R_3$ is hydrogen atom and $R_4$ is said alkyl group or said alkenyl group, and when $R_1$ is said group

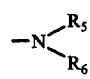

and $R_2$ is nitro group, $R_3$ and $R_4$ are the same as defined above with respect to the $R_5$ and $R_6$.

They are highly effective in the treatment of coccidiosis, especially that caused by the protozoa belonging to the species *Eimeria tenella* or *E. necatrix*.

60 Claims, No Drawings

PYRIDINE SULFONAMIDES AND THEIR USE AS ANTICOCCIDIAL AGENTS

This invention relates to a new group of pyridine derivatives and their use as an anticoccidial agent.

More particularly, it is concerned with a new pyridine derivative having the formula

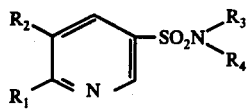  (I)

wherein

R$_1$ represents hydrogen atom, amino group or a group

in which R$_5$ and R$_6$ may be the same or different and each represents an alkyl group of 1 to 4 carbon atoms or R$_5$ is hydrogen atom and R$_6$ represents an alkyl group of 1 to 4 carbon atoms, an alkenyl group of 3 or 4 carbon atoms or a benzyl group optionally substituted with halogen, cyano, alkyl of 1 to 4 carbon atoms or alkoxy of 1 to 4 carbon atoms;

R$_2$ represents nitro group, amino group or an alkylamino group of 1 to 3 carbon atoms;

R$_3$ and R$_4$ individually represent hydrogen atom, an alkyl group of 1 to 4 carbon atoms, an alkoxyalkyl group which has 1 to 4 carbon atoms in the alkoxy moiety and 2 to 4 carbon atoms in the alkyl moiety, an alkenyl group of 3 or 4 carbon atoms, an alkanoyl group of 1 to 18 carbon atoms or a benzyl group optionally substituted with halogen, cyano, alkyl of 1 to 4 carbon atoms or alkoxy of 1 to 4 carbon atoms, provided that when R$_1$ is hydrogen atom and R$_2$ is nitro group, R$_3$ and R$_4$ may be the same or different and each represents said alkyl group or said alkoxyalkyl group or R$_3$ is hydrogen atom and R$_4$ is hydrogen atom, said alkyl group, said alkoxyalkyl group, said alkenyl group, said alkanoyl group or said benzyl group, when R$_1$ is hydrogen atom and R$_2$ is amino group or said alkylamino group, R$_3$ and R$_4$ individually is hydrogen atom or they may be the same or different and each represents said alkyl group, when R$_1$ is amino group and R$_2$ is nitro group, R$_3$ and R$_4$ may be the same or different and each represents said alkyl group or R$_3$ is hydrogen atom and R$_4$ is said alkyl group or said alkenyl group, and when R$_1$ is said group

and R$_2$ is nitro group, R$_3$ and R$_4$ are the same as defined above with respect to the R$_5$ and R$_6$.

It is also concerned with a new composition containing, as an active anticoccidial agent, the pyridine derivative (I).

Coccidiosis is a common and widespread disease of poultries, especially chickens and turkeys, and domestic animals such as rabbits, goats, sheep, and cattles, which disease is caused by a kind of protozoa belonging to class Sporozoa, order Coccidia, family Eimeriidae.

Coccidiosis of poultries and domestic animals is caused mainly by the protozoa belonging to genus Eimeria, which disease is classified to an acute type and a chronic one.

The former is caused by such species as *E. tenella* and *E. necatrix*, and the characteristic feature of the disease is a copious bloody discharges from the ceca and small intestine of diseased poultries, which often die within a day or two.

The latter is caused by such species as *E. acervulina*, *E. maxima*, *E. brunetti*, *E. praecox*, *E. hagani*, *E. mitis* and *E. mivati*, and the characteristic feature of the disease is that the mortality of diseased poultries is rather few, whereas a poor weight gain, a reduced feed efficiency and a reduced efficiency of egg-production are commonly observed.

Infant rabbits as well as cattles, sheep and goats sometimes cause severe lesions by parasite Eimeria within their livers and intestines.

Oocysts of coccidia are excreted from an infected animal with feces, and spores having infectivity are produced within 24 - 48 hours under suitable conditions, which spores enter into a non-infected animal orally.

Oocysts grow at first asexually within the cells of the ceacum or small intestine of the host animal, during which time the heaviest symptoms is observed. Then, they grow sexually and are excreted with the feces of the host animal and they exhibit an awful communicability.

The elimination or control of coccidiosis is, therefore, of paramount importance particularly in the poultry industry.

There have been proposed much preventive and curative methods for coccidiosis. One of them is a development in chemotherapeutic agents such as sulfa drugs, arsenic compounds, nitrofuran derivatives, nitrophenide, Nicarbazine, Zoalane, pyrimidine derivatives (anti-thiamines), quinoline derivatives, guanidine derivatives, various antibiotics and so on.

But they have some defects; i.e. weak activity, narrow anti-protozoal spectrum, lack of security for animals or acquired resistance to the drugs by protozoa, respectively. Therefore, treatment with the hither-to-known anticoccidial agent is not satisfactory.

It was reported in Nature 208, 397 (1965) and U.S. Pat. No. 3,202,576 that 3-sulfamoylpyridine, 4-methyl-3-sulfamoylpyridine and so on are effective against chronic coccidiosis caused by *Eimeria acervulina*, but ineffective against acute coccidiosis caused by *Eimeria tenella* etc.

As a result of our further studies on pyridine derivatives and their anticoccidial activities, we have found that the new pyridine derivatives (I) surprisingly show a remarkably high anticoccidial activity, specifically, against the acute coccidiosis caused by *E. tenella, E. necatrix* etc. and they are also highly effective against those strains resistant to known various thiamine type anticoccidial agents.

It is, accordingly, a primary object of this invention to provide a new class of the pyridine derivatives (I) which are highly effective against specific coccidiosis.

It is another object of this invention to provide an anticoccidial composition which are highly effective in treating and preventing specific coccidiosis.

Another objects and advantages will become apparent from the following detailed description of this invention.

In the above formula (I), $R_1$ may be exemplified by hydrogen atom, amino group, methylamino, ethylamino, n-propyl- or isopropylamino, n-butyl-, isobutyl-, sec-butyl- or tert-butylamino, allylamino, 3-butenylamino, dimethylamino, diethylamino, di-n-propylamino, di-isopropylamino, ethylmethylamino, methylpropylamino, benzylamino, o-, m- or p-chlorobenzylamino, o-, m- or p-cyanobenzylamino, o-, m- or p-methylbenzylamino, o-, m- or p-n-butylbenzylamino, o-, m- or p-methoxybenzylamino, o-, m- or p-n-butoxybenzylamino group etc. $R_2$ may be exemplified by nitro group, amino group, methylamino, ethylamino, n-propylamino, isopropylamino etc. $R_3$ and $R_4$ individually may be exemplified by hydrogen atom, methyl, ethyl, n-propyl, i-propyl, n-butyl, i-butyl, sec-butyl, 2-methoxyethyl, 2-ethoxyethyl, 2-n-propoxyethyl, 2-n-butoxyethyl, 2-i-butoxyethyl, 3-methoxypropyl, 2-methoxypropyl, 3-ethoxypropyl, 3-n-propoxypropyl, 3-i-propoxypropyl, 4-methoxybutyl, 4-ethoxybutyl, 4-n-propoxybutyl, allyl, 3-butenyl, formyl, acetyl, propionyl, butyryl, isobutyryl, valeryl, isovaleryl, 2-methylbutyryl, hexanoyl, heptanoyl, octanoyl, nonanoyl, decanoyl, undecanoyl, lauroyl, myristoyl, palmitoyl, stearoyl, benzyl, (o-, m-, p-)methylbenzyl, methylbenzyl, 2,5-dimethylbenzyl, (o-, m-, p-)methoxybenzyl group etc.

In one aspect of this invention, there is provided a new class of the pyridine derivatives (I), which involve the following 4 groups of pyridine derivatives.

Group A .... The pyridine derivatives of the formula (I) wherein $R_1$ is hydrogen atom, $R_2$ is nitro group, $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group, said alkenyl group, said alkanoyl group or said benzyl group.

Group B .... The pyridine derivatives of the formula (I) wherein $R_1$ is hydrogen atom, $R_2$ is amino group or said alkylamino group, $R_3$ and $R_4$ individually is hydrogen atom or they may be the same or different and each represents said alkyl group.

Group C .... The pyridine derivatives of the formula (I) wherein $R_1$ is amino group, $R_2$ is nitro group, $R_3$ and $R_4$ may be the same or different and each represents said alkyl group or $R_3$ is hydrogen atom and $R_4$ is said alkyl group or said alkenyl group.

Group D .... The pyridine derivatives of the formula (I) wherein $R_1$ is said group

and $R_2$ is nitro group, $R_3$ and $R_4$ are the same as defined above with respect to the $R_5$ and $R_6$.

In view of anticoccidial activities, there may be mentioned the following groups as respective preferable ones of the above Groups A, B, C and D.

The preferable Group A includes the pyridine derivatives of the formula (I) wherein $R_1$ is hydrogen atom, $R_2$ is nitro group, and $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group or an alkanoyl group of 2 to 8 carbon atoms.

The preferable Group B includes the pyridine derivatives of the formula (I) wherein $R_1$ is hydrogen atom, $R_2$ is amino group and $R_3$ and $R_4$ may be the same or different and each represents methyl group or ethyl group.

The preferable Group C includes the pyridine derivatives of the formula (I) wherein $R_1$ is amino group, $R_2$ is nitro group and $R_3$ and $R_4$ may be the same or different and each represents methyl group or ethyl group or $R_3$ is hydrogen atom and $R_4$ is methyl group or ethyl group.

The preferable Group D includes the pyridine derivatives of the formula (I) wherein $R_1$ is the group

in which $R_5$ and $R_6$ may be the same or different and each represents methyl group or ethyl group or $R_5$ is hydrogen atom and $R_6$ is methyl group or ethyl group, $R_2$ is nitro group, $R_3$ and $R_4$ are as defined above with respect to the above $R_5$ and $R_6$.

Still more preferable group of the pyridine derivatives (I) includes those wherein $R_1$ is hydrogen atom, $R_2$ is nitro group and $R_3$ and $R_4$ may be the same or different and each represents said alkyl group or said alkoxyalkyl group or $R_3$ is hydrogen atom and $R_4$ is hydrogen atom, said alkyl group or said alkoxyalkyl group; wherein $R_1$ is amino group, $R_2$ is nitro group and $R_3$ and $R_4$ may be the same or different and each represents methyl group or ethyl group or $R_3$ is hydrogen atom and $R_4$ is methyl group or ethyl group; and wherein $R_1$ is dimethylamino group or methylamino group, $R_2$ is nitro group and $R_3$ and $R_4$ individually represent methyl group or $R_3$ is hydrogen atom and $R_4$ is methyl group.

The most preferable group of the pyridine derivatives (I) includes those wherein $R_1$ is hydrogen atom, $R_2$ is nitro group and $R_3$ and $R_4$ may be the same or different and each represents said alkyl group or said alkoxyalkyl group or $R_3$ is hydrogen atom and $R_4$ is hydrogen atom, said alkyl group or said alkoxyalkyl group; and wherein $R_1$ is dimethylamino group or methylamino group, $R_2$ is nitro group and $R_3$ and $R_4$ individually represent methyl group or $R_3$ is hydrogen atom and $R_4$ is methyl group.

Of the pyridine derivatives of the formula (I), representative examples thereof are listed below, but they are not intended to be limiting the scope of this invention.

| Compound No. | Chemical Name |
|---|---|
| 1. | N-methyl 5-nitro-3-pyridinesulfonamide |
| 2. | N-ethyl 5-nitro-3-pyridinesulfonamide |
| 3. | N-n-propyl 5-nitro-3-pyridinesulfonamide |
| 4. | N-isopropyl 5-nitro-3-pyridinesulfonamide |
| 5. | N-n-butyl 5-nitro-3-pyridinesulfonamide |
| 6. | N-isobutyl 5-nitro-3-pyridinesulfonamide |
| 7. | N-sec-butyl 5-nitro-3-pyridinesulfonamide |
| 8. | N-ally 5-nitro-3-pyridinesulfonamide |
| 9. | N,N-dimethyl 5-nitro-3-pyridinesulfonamide |
| 10. | N,N-diethyl 5-nitro-3-pyridinesulfonamide |
| 11. | N,N-di-n-propyl 5-nitro-3-pyridinesulfonamide |
| 12. | N,N-di-isopropyl 5-nitro-3-pyridinesulfonamide |
| 13. | N-ethyl-N-methyl 5-nitro-3-pyridinesulfonamide |
| 14. | N-methyl-N-n-propyl 5-nitro-3-pyridinesulfonamide |
| 15. | N-ethyl-N-n-propyl 5-nitro-3-pyridinesulfonamide |
| 16. | N-n-butyl-N-methyl 5-nitro-3-pyridinesulfonamide |
| 17. | N-n-butyl-N-ethyl 5-nitro-3-pyridinesulfonamide |
| 18. | N-(2-methoxyethyl) 5-nitro-3-pyridinesulfonamide |
| 19. | N-(2-ethoxyethyl) 5-nitro-3-pyridinesulfonamide |
| 20. | N-(2-n-propoxyethyl) 5-nitro-3-pyridinesulfonamide |
| 21. | N-(2-n-butoxyethyl) 5-nitro-3-pyridinesulfonamide |

-continued

| Compound No. | Chemical Name |
|---|---|
| 22. | N-(2-isobutoxyethyl) 5-nitro-3-pyridinesulfonamide |
| 23. | N-(2-methoxyropyl) 5-nitro-3-pyridinesulfonamide |
| 24. | N-(3-methoxypropyl) 5-nitro-3-pyridinesulfonamide |
| 25. | N-(3-ethoxypropyl) 5-nitro-3-pyridinesulfonamide |
| 26. | N-(3-n-propoxypropyl) 5-nitro-3-pyridinesulfonamide |
| 27. | N-(3-isopropoxypropyl) 5-nitro-3-pyridinesulfonamide |
| 28. | N-(4-methoxybutyl) 5-nitro-3-pyridinesulfonamide |
| 29. | N-(4-ethoxbutyl) 5-nitro-3-pyridinesulfonamide |
| 30. | N-(4-n-propoxybutyl) 5-nitro-3-pyridinesulfonamide |
| 31. | N-(2-methoxyethyl-N-methyl 5-nitro-3-pyridinesulfonamide |
| 32. | N-(2-ethoxyethyl)-N-methyl 5-nitro-3-pyridinesulfonamide |
| 33. | N-(2-methoxyethyl)-N-ethyl 5-nitro-3-pyridinesulfonamide |
| 34. | N-(2-ethoxyethyl)-N-ethyl 5-nitro-3-pyridinesulfonamide |
| 35. | N,N-di-(2-methoxyethyl) 5-nitro-3-pyridinesulfonamide |
| 36. | N,N-di-(2-ethoxyethyl) 5-nitro-3-pyridinesulfonamide |
| 37. | N-benzyl 5-nitro-3-pyridinesulfonamide |
| 38. | N-(o-chlorobenzyl) 5-nitro-3-pyridinesulfonamide |
| 39. | N-(m-chloroenzyl) 5-nitro-3-pyridinesulfonamide |
| 40. | N-(p-chloroenzyl) 5-nitro-3-pyridinesulfonamide |
| 41. | N-(p-cyanobenzyl) 5-nitro-3-pyridinesulfonamide |
| 42. | N-(o-methylbenzyl) 5-nitro-3-pyridinesulfonamide |
| 43. | N-(m-methylbenzyl) 5-nitro-3-pyridinesulfonamide |
| 44. | N-(p-methylbenzyl) 5-nitro-3-pyridinesulfonamide |
| 45. | N-(p-n-butylbenzyl) 5-nitro-3-pyridinesulfonamide |
| 46. | N-(2,5-dimethylbenzyl) -nitro-3-pyridinesulfonamide |
| 47. | N-(o-methoxybenzyl) 5-nitro-3-pyridinesulfonamide |
| 48. | N-(m-methoxybenzyl) 5-nitro-3-pyridinesulfonamide |
| 49. | N-(p-methoxybenzyl) 5-nitro-3-pyridinesulfonamide |
| 50. | N-(p-butoxybenzyl) 5-nitro-3-pyridinesulfonamide |
| 51. | N-(3-butenyl) 5-nitro-3-pyridinesulfonamide |
| 52. | N-formyl 5-nitro-3-pyridinesulfonamide |
| 53. | N-acetyl 5-nitro-3-pyridinesulfonamide |
| 54. | N-propionyl 5-nitro-3-pyridinesulfonamide |
| 55. | N-butyryl 5-nitro-3-pyridinesulfonamide |
| 56. | N-isobutyryl 5-nitro-3-pyridinesulfonamide |
| 57. | N-valeryl 5-nitro-3-pyridinesulfonamide |
| 58. | N-isovaleryl 5-nitro-3-pyridinesulfonamide |
| 59. | N-hexanoyl 5-nitro-3-pyridinesulfonamide |
| 60. | N-2-methylbutyryl 5-nitro-3-pyridinesulfonamide |
| 61. | N-heptanoyl 5-nitro-3-pyridinesulfonamide |
| 62. | N-octanoyl 5-nitro-3-pyridinesulfonamide |
| 63. | N-nonanoyl 5-nitro-3-pyridinesulfonamide |
| 64. | N-decanoyl 5-nitro-3-pyridinesulfonamide |
| 65. | N-undecanoyl 5-nitro-3-pyridinesulfonamide |
| 66. | N-lauroyl 5-nitro-3-pyridinesulfonamide |
| 67. | N-myristoyl 5-nitro-3-pyridinesulfonamide |
| 68. | N-palmitoyl 5-nitro-3-pyridinesulfonamide |
| 69. | N-stearoyll 5-nitro-3-pyridinesulfonamide |
| 70. | 5-nitro-3-pyridinesulfonamide |
| 71. | 5-amino-3-pyridinesulfonamide |
| 72. | N,N-dimethyl 5-amino-3-pyridinesulfonamide |
| 73. | N,N-diethyl 5-amino-3-pyridinesulfonamide |
| 74. | N,N-di-n-propyl 5-amino-3-pyridinesulfonamide |
| 75. | N,N-di-isopropyl 5-amino-3-pyridinesulfonamide |
| 76. | N-ethyl-N-methyl 5-amino-3-pyridinesulfonamide |
| 77. | N-methyl-N-n-propyl 5-amino-3-pyridinesulfonamide |
| 78. | N-ethyl-N-n-propyl 5-amino-3-pyridinesulfonamide |
| 79. | 5-methylamino-3-pyridinesulfonamide |
| 80. | N,N-dimethyl 5-methylamino-3-pyridinesulfonamide |
| 81. | N,N-diethyl 5-methylamino-3-pyridinesulfonamide |
| 82. | N,N-di-n-propyl 5-methylamino-3-pyridinesulfonamide |
| 83. | 5-ethylamino-3-pryidinesulfonamide |
| 84. | N,N-dimethyl 5-ethylamino-3-pyridinesulfonamide |
| 85. | N,N-diethyl 5-ethylamino-3-pyridinesulfonamide |
| 86. | N,N-di-n-propyl 5-ethylamino-3-pyridinesulfonamide |
| 87. | N,N-di-inopropyl 5-ethylamino-3-pyridinesulfonamide |
| 88. | N-ethyl-N-methyl 5-ethylamino-3-pyridinesulfonamide |
| 89. | 5-n-propylamino-3-pyridinesulfonamide |
| 90. | N,N-dimethyl 5-n-propylamino-3-pyridinesulfonamide |
| 91. | N,N-diethyl 5-n-propylamino-3-pyridnesulfonamide |
| 92. | N,N-di-n-propyl 5-n-propylamino-3-pyridinesulfonamide |
| 93. | 5-isopropylamino-3-pyridinesulfonamide |
| 94. | N-methyl 6-amino-5-nitro-3-pyridinesulfonamide |
| 95. | N-ethyl 6-amino-5-nitro-3-pyridinesulfonamide |
| 96. | N-n-propyl 6-amino-5-nitro-3-pyridinesulfonamide |
| 97. | N-isopropyl 6-amino-5-nitro-3-pyridinesulfonamide |
| 98. | N-n-butyl 6-amino-5-nitro-3-pyridinesulfonamide |
| 99. | N-isobutyl 6-amino-5-nitro-3-pyridinesulfonamide |
| 100. | N-sec-butyl 6-amino-5-nitro-3-pyridinesulfonamide |
| 101. | N-allyl 6-amino-5-nitro-3-pyridinesulfonamide |
| 102. | N,N-dimethyl 6-amino-5-nitro-3-pyridinesulfonamide |
| 103. | N,N-diethyl 6-amino-5-nitro-3-pyridinesulfonamide |
| 104. | N,N-di-n-propyl 6-amino-5-nitro-3-pyridinesulfonamide |
| 105. | N,N-di-isopropyl 6-amino-5-nitro-3-pyridinesulfonamide |
| 106. | N-ethyl-N-methyl 6-amino-5-nitro-3-pyridinesulfonamide |
| 107. | N-methyl-N-n-propyl 6-amino-5-nitro-3-pyridinesulfonamide |
| 108. | N-n-butyl-N-methyl 6-amino-5nitro-3-pyridinesulfonamide |
| 109. | N-n-butyl-N-ethyl 6-amino-5-nitro-3-pyridinesulfonamide |
| 110. | N-(3-butenyl) 6-(3-butenylamino)-5-nitro-3-pyridinesulfonamide |
| 111. | N-methyl 6-methylamino-5-nitro-3-pyridinesulfonamide |
| 112. | N-ethyl 6-ethylamino-5-nitro-3-pyridinesulfonamide |
| 113. | N-n-propyl 6-n-propylamino-5-nitro-3-pyridinesulfonamide |
| 114. | N-isopropyl 6-isopropylamino-5-nitro-3-pyridinesulfonamide |
| 115. | N-n-butyl 6-n-butylamino-5-nitro-3-pyridinesulfonamide |
| 116. | N-isobutyl 6-isobutylamino-5-nitro-3-pyridinesulfonamide |
| 117. | N-sec-butyl 6-n-butylamino-5-nitro-3-pyridinesulfonamide |
| 118. | N-allyl 6-allylamino-5-nitro-3-pyridinesulfonamide |
| 119. | N,N-dimethyl 6-dimethylamino-5-nitro-3-pyridinesulfonamide |
| 120. | N,N-diethyl 6-diethylamino-5-nitro-3-pyridinesulfonamide |
| 121. | N,N-di-n-propyl 6-di-n-propylamino-5-nitro-3-pyridinesulfonamide |
| 122. | N,N-di-isopropylamino-5-nitro-3-pyridinesulfonamide |
| 123. | N-ethyl-N-methyl 6-ethylmethylamino-5-nitro-3-pyridinesulfonamide |
| 124. | N-methyl-N-n-propyl 6-methyl-n-propylamino-5-nitro-3-pyridinesulfonamide |
| 125. | N-benzyl 6-benzylamino-5-nitro-3-pyridinesulfonamide |
| 126. | N-(o-chlorobenzyl) 6-(o-chlorobenzylamino)-5-nitro-3-pyridinesulfonamide |
| 127. | N-(m-chlorobenzyl) 6-(m-chlorobenzylamino)-5-nitro-3-pyridinesulfonamide |
| 128. | N-(p-chlorobenzyl) 6-(p-chlorobenzylamino)-5-nitro-3-pyridinesulfonamide |
| 129. | N-(p-cyanobenzyl) 6-(p-cyanobenzylamino)-5-nitro-3-pyridinesulfonamide |
| 130. | N-(o-methylbenzyl) 6-(o-methylbenzylamino)-5-nitro-3-pyridinesulfonamide |
| 131. | N-(m-methylbenzyl)-5-nitro-3-pyridinesulfonamide |
| 133. | N-(o-methylbenzyl) 6-(o-methoxybenzylamino)-5-nitro-3-pyridinesulfonamide |
| 134. | N-(m-methoxybenzyl) 6-(m-methoxybenzylamino)- |
| 135. | N-(p-methoxybenzyl) 6-(p-methoxybenzylamino)-5-nitro-3-pyridinesulfonamide |

It is to be noted that the above-defined Compound Nos. will be frequently referred to hereinbelow.

Of the above-listed compounds, there are mentioned the following compounds as a preferable group in view of their anticoccidial activities.

Compound Nos. 1, 2, 3, 9, 17, 19, 27, 34, 37, 53, 62, 70, 71, 72, 73, 85, 94, 95, 102, 103, 111, 112, 115, 119, 120, 125, 128, and 135.

The most preferable group of the above-listed compounds are as follows:

Compound Nos. 1, 2, 9, 19, 27, 34, 70, 94, 95, 102, 111, 119.

The pyridine compounds of the formula (I) which may be employed in the present invention may be prepared, for instance, by any of the processes as illustratively shown hereunder.

Process I

In case where $R_1$ is hydrogen atom, $R_2$ is nitro group and $R_3$ and $R_4$ individually represent hydrogen atom or $R_3$ is hydrogen atom and $R_4$ is said alkanoyl group.

As illustrated below, 3-pyridinesulfonylchloride (II) [described in Chem. Abstract 37, 6652⁹ (1943)] was heated with bromine to synthesize 5-bromo-3-pyridinesulfonylchloride (III) which was then reacted with ammonia to prepare compounds (IV) and (V), followed by the oxidation by a mixture of hydrogen peroxide and fuming sulfuric acid to prepare the compound (VI). The compound (VI) was reacted with an anhydride ($R_2O$; R represents an alkanoyl group) at 10° – 150° C in the presence of a catalytic amount of sulfuric acid, toluene sulfonic acid, etc. to obtain the desired compound (VII). The compound (VII) can also be obtained by bringing the compound (VI) into contact with acid chloride (RCl; R has the same meaning as above) in pyridine or in an aqueous solution of alkali carbonate.

ing sulfuric acid to (X) which is chlorinated with $PCl_5$ and further reacted with an amine

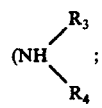

$R_3$ and $R_4$ have the same meanings as above) to obtain the desired compound (XII).

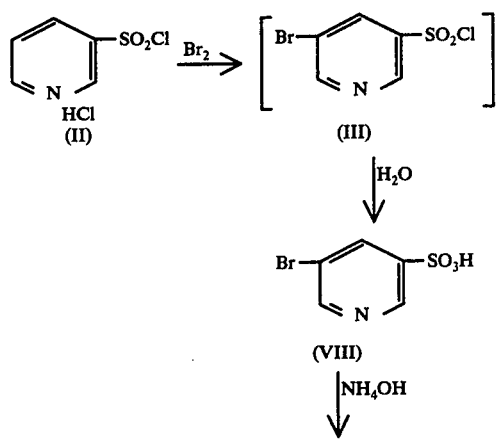

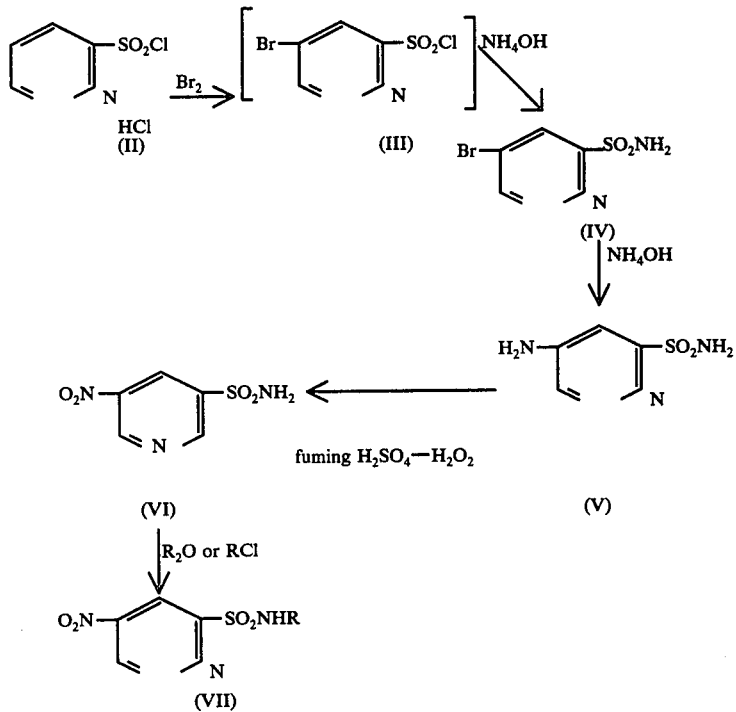

Process II

In case where $R_1$ is hydrogen atom, $R_2$ is nitro group and $R_3$ and $R_4$ are other groups than those defined above with respect to the Process I.

As illustrated below, 3-pyridinesulfonylchloride (II) [described in Chemical Abstract 37, 6652⁹ (1943)] was heated with bromine to synthesize 5-bromo-3-pyridinesulfonyl chloride (III) which was then hydrolized to 5-bromo-3-pyridinesulfonic acid (VIII). The compound (VIII) is subjected to amination and then oxidized with a mixture of hydrogen peroxide and fum-

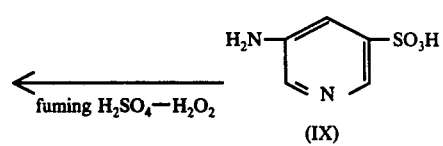

-continued

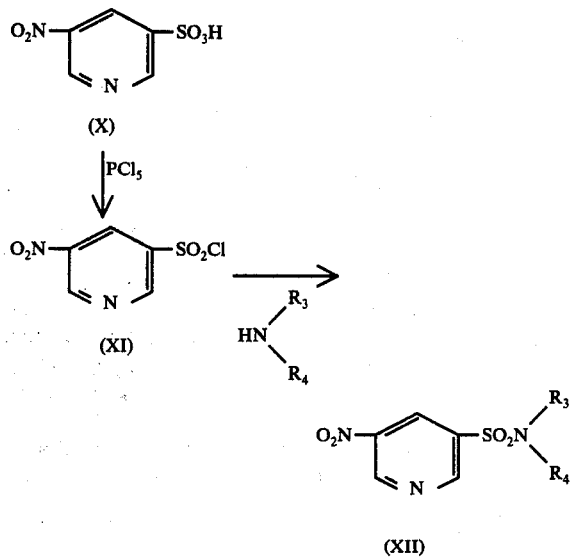

Some examples of the above Processes I and II are given below.

EXAMPLE 1

5-Nitro-3-pyridinesulfonamide

A mixture of 2.14g. of 3-pyridinesulfonylchloride and 1.6g. of bromine was heated at 110° – 120° C. for 8 hours. After cooling, 30 ml. of 20% aqueous ammonia was added to the reaction mixture and the resulting mixture was stirred for 30 minutes. The mixture was neutralized with conc. hydrochloric acid, saturated with sodium chloride and extracted with ethyl acetate. The extract was dried and the solvent was distilled off. The residue was recrystallized from ethanol-petroleum ether to give 1.3g. of 5-bromo-3-pyridinesulfonamide. m.p. 178° – 179° C.

A mixture of 7.4g. of the sulfonamide obtained above, 15 ml. of 28% aqueous ammonia and 0.8g. of cupric sulfate was heated in a sealed tube at 180° C. for 20 hours. After cooling, an aqueous solution of sodium sulfide was added to the reaction mixture until any cupric sulfide was not further precipitated. The precipitate was filtered off and the aqueous layer was concentrated and extracted with ethyl acetate. The extract was dried and the solvent was distilled off. The resulting crystalline substance was recrystallized from ethanol-n-hexane to give 3.5g. of 5-amino-3-pyridinesulfonamide. m.p. 177° – 179° C.

To a mixture of 60 ml. of fuming sulfuric acid and 30 ml. of 30% hydrogen peroxide was slowly added 3.0g. of the sulfonamide obtained above. The mixture was stirred at room temperature for 48 hours and poured into ice-water. The resulting mixture was neutralized with sodium carbonate and extracted with ethyl acetate. The extract was dried and the solvent was distilled off. The crystalline residue was recrystallized from ethyl acetate-n-hexane to give 0.8g. of 5-nitro-3-pyridinesulfonamide. m.p. 168° C.

EXAMPLE 2

N-Acetyl 5-nitro-3-pyridinesulfonamide

A mixture of 0.5g. of 5-nitro- 3-pyridinesulfonamide, 2 ml. of acetic anhydride and 2 drops of conc. sulfuric acid was stirred at 90° C. for 1 hour. The solvent was then distilled off from the reaction mixture and the crystalline residue was recrystallized from ethanol to give 0.36g. of the desired product. m.p. 176° – 178° C.

EXAMPLE 3

N-Acetyl 5-nitro-3-pyridinesulfonamide

To 10 ml. of a 10% aqueous sodium carbonate solution of 0.5g. of 5-nitro-3-pyridinesulfonamide was added dropwise 1g. of acetyl chloride at 0° C. The mixture was stirred at room temperature for 2 hours and extracted with ethyl acetate. The extract was purified by silica gel chromatography to give 0.26g. of the desired product. m.p. 176° – 178° C.

Following the above-mentioned procedures, there was obtained the following compound. N-Octanoyl 5-nitro-3-pyridinesulfonamide m.p. 103° – 105° C.

EXAMPLE 4

N-Ethyl 5-nitro-3-pyridinesulfonamide

A mixture of 3g. of 3-pyridinesulfonic acid and 8.5g. of phosphorous pentachloride was heated at 120° C for 1.5 hours. Upon cooling to room temperature, the mixture solidified. Chloroform was added thereto and dry hydrogen chloride gas was introduced. The resulting precipitate was collected by filtration and dried. The crystalline substance obtained was heated with bromine (4g.) at 120° C. for 8 hours and water (60 ml.) was added to the mixture. After stirring at 80° C. for 2 hours, the solution was concentrated. On addition of acetone, 2g. of 5-bromo-3-pyridinesulfonic acid was obtained.

A mixture of 1.3g. of 5-bromo-3-pyridinesulfonic acid, cupric sulfate pentahydrate (2.3g.) and 27% aqueous ammonia (30 ml.) was heated in a sealed tube at 170° – 180° C. for 20 hours. After cooling, a saturated aqueous solution of sodium sulfide was added to the mixture and the resulting precipitate of cupric sulfide was filtered off. The filtrate was concentrated and acidified with conc. hydrochloric acid to give 1.0g. of 5-amino-3-pyridinesulfonic acid. m.p. above 300° C.

To a mixture of fuming sulfuric acid (10 ml.) and 30% $H_2O_2$ (6 ml.), was added dropwise a solution of 1g. of 5-amino-3-pyridinesulfonic acid in conc. sulfuric acid (4 ml.) at a temperature of below 20° C. The mixture was stirred for 16 hours and then poured into ice water. After adjusting the medium to be slightly acidic with sodium carbonate, the solvent was removed by evaporation. The residue was extracted with ethyl alcohol and the extract was evaporated to dryness to give 0.6g. of light yellow 5-nitro-3-pyridinesulfonic acid.

A mixture of 0.5g. of 5-nitro-3-pyridinesulfonic acid, 0.5g. of phosphorous pentachloride and 15 ml. of phosphorous oxychloride was heated under reflux for 6 hours. After removing the solvent by evaporation, dry chloroform was added to give a powdery crystal. After adding the crystal to 2.5 ml. of 20% ethyl amine under cooling, the mixture was stirred for 1 at room temperature. Then, the mixture was diluted with water and extracted with ethyl acetate. The extact was washed with water and dried. After removing the solvent by evaporation and purification by chromatography, 0.2g. of the desired compound was obtained. m.p. 117°–118° C. Similarly, the following compounds were synthesized.

N-Methyl 5-nitro-3-pyridinesulfonamide m.p. 136°–137° C.

N-Propyl 5-nitro- 3-pyridinesulfonamide m.p. 111°–112° C

N-(2-Ethoxyethyl) 5-nitro-3-pyridinesulfonamide m.p. 72°–73° C.

N-(3-Isopropoxypropyl) 5-nitro-3-pyridinesulfonamide m.p. 71°–73° C.

N-Benzyl 5-nitro-3-pyridinesulfonamide m.p. 132°–134° C.

N,N-Dimethyl 5-nitro-3-pyridinesulfonamide m.p. 159°– 160° C.

N-n-Butyl-N-ethyl 5-nitro- 3-pyridinesulfonamide m.p. 67°–69° C.

N-Ethyl-N-(2-ethoxyethyl) 5-nitro-3-pyridinesulfonamide m.p. 69°–70° C.

Process III In case where $R_1$ is hydrogen atom, $R_3$ and $R_4$ individually represent hydrogen atom or they may be the same or different and each represents said alkyl group.

As illustrated below, the 5-bromo-3-pyridinesuflonylchloride (III) was synthesized in the same manner as seen in the Process I, reacted with an amine of the formula

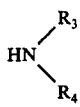

wherein $R_3$ and $R_4$ are as defined above followed by reaction with ammonia or an alkylamine in the presence of $CuSO_4$ to produce the compound (XIV).

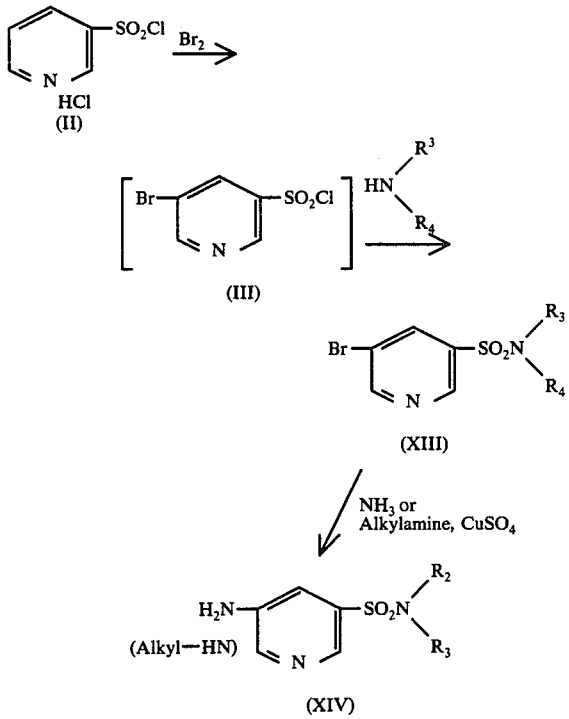

Some examples of the Process III are given below.

EXAMPLE 5

N,N-Diethyl 5-ethylamino-3-pyridinesulfonamide

A mixture of 2.1g. of 3-pyridinesulfonylchloride and 1.6g. of bromine was heated at 110°–120° C. for 8 hours. After cooling, 15 ml. of diethylamine was added thereto and the resulting mixture was stirred at room temperature for 3 hours. The mixture was then diluted with ice-water and extracted with chloroform. The extract was washed with water and dried. The solvent was distilled off and the oily residue thus obtained was crystallized from ethyl acetate-n-hexane to give 1.8g. of N,N-diethyl 5-bromo-3-pyridinesulfonamide. m.p. 70°–72° C.

A mixture of 1.9g. of the sulfonamide obtained above, 0.2g. of cupric sulfate and 15 ml. of ethylamine was heated to 170° C. in a sealed tube for 20 hours. After cooling, an aqueous solution of sodium sulfide was added to the reaction mixture until any cupric sulfide was not further precipitated. The precipitated was filtered off and the filtrate was extracted with ethyl acetate. The extract was dried and the solvent was distilled off. The oily residue was purified by silica gel chromatography and recrystallized from ethyl acetate-n-hexane to give 0.2g. of the desired product. m.p. 58°–60° C. Similarly, the following compounds were synthesized.

N,N-Diethyl 5-amino-3-pyridinesulfonamide m.p. 122°–124° C.

5-Amino-3-pyridinesulfonamide m.p. 177°–179° C.

Process IV

In case where $R_1$ is amino group, $R_2$ is nitro group and $R_3$ and $R_4$ may be the same or different and each represents said alkyl group or $R_3$ is hydrogen atom and $R_4$ is said alkyl group or said alkenyl group.

As illustrated below. 6-amino-5-nitro-3-pyridinesulfonic acid is reacted with phosphorus pentachloride according to the method disclosed in J. Am. Chem. Soc. 79, 6421 (1957) followed by reaction with an amine of the formula

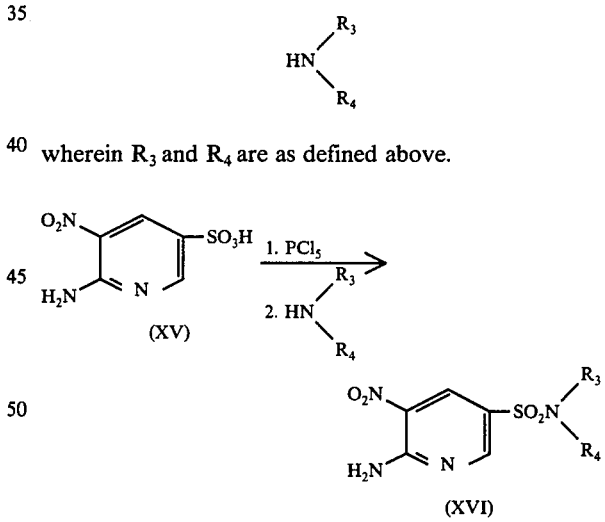

wherein $R_3$ and $R_4$ are as defined above.

EXAMPLE 6

N,N-Dimethyl 6-amino-5-nitro-3-pyridinesulfonamide

A mixture of 1.9g. of 6-amino-5-nitro-3-pyridinesulfonic acid and 3.6g. of phosphorus pentachloride was heated at 170°–180° C. for 3 hours. After cooling, dry benzene was added thereto and the mixture was filtered. The filtrate was distilled off under reduced pressure to give 1.47g. of an oily substance, which was then dissolved in a mixture of 8.7 ml. of dioxane and 8.7 ml. of water. To the solution was added dropwise 12.9 ml. of dimethylamine under cooling. The resulting mixture was stirred at room temperature for 1 hour, diluted with water, adjusted to pH 7 with hydrochloric acid and extracted with ethyl acetate. The extract was dried and the solvent was distilled off. The residue was purified by silica gel chromatography and recrystallized from ethyl acetate to give 0.6g. of the desired produce as yellow crystals. m.p. 212°–214° C.

Similarly, the following compounds were synthesized. N-Ethyl 6-amino-5-nitro-3-pyridinesulfonamide m.p. 208° C.

N-Methyl 6-amino-5-nitro-3-pryridinesulfonamide m.p. 205°–206.5° C.

N,N-Diethyl 6-amino-5-nitro-3-pyridinesulfonamide m.p. 164°–166° C.

Process V

In case where $R_1$ is the group

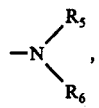

$R_2$ is nitro group and $R_3$ and $R_4$ may be the same or different and each represents said alkyl group or $R_3$ is hydrogen atom and $R_4$ is said alkyl group, said alkenyl group or said benzyl group.

As illustrated below, 6-chloro-5-nitro-3-pyridinesulfonylchloride (Rocz. Chem. 34, 1149 (1960)) is reacted with an amine of the formula

wherein $R_3$ and $R_4$ are as defined above to produce the desired compound (XVIII).

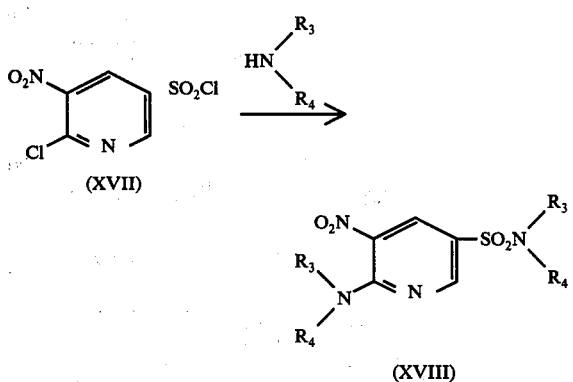

Some examples of the Process V are given below.

EXAMPLE 7

N-Ethyl 6-ethylamino-5-nitro-3-pyridinesulfonamide

To a mixture of 6g. of a 70% aqueous solution of ethylamine and 20 ml. of ether was added a solution of 0.6g. of 6-chloro-5-nitro-3-pyridinesulfonyl chloride in 20 ml. of acetone at −10° C. After stirring for 1 hour, the solvent was distilled off below 30° C., the residue was added to ice-water and the mixture was extracted with ethyl acetate. The solvent was distilled off from the extract and the crystalline substance was purified by silica gel chromatography and then recrystallized from ethyl acetate-n-hexane to give 0.3g. of the desired product. m.p. 153°–155°C. Similarly, the following compounds were synthesized. N-Methyl 6-methylamino-5-nitro-3-pyridinesulfonamide m.p. 186°–188° C.

N-n-Butyl 6-n-butylamino-5-nitro- 3-pyridinesulfonamide m.p. 104°–106° C.

N,N-Dimethyl 6-dimethylamino-5-nitro-3-pyridinesulfonaide m.p. 146°–148° C.

N,N-Diethyl 6-diethlyamino-5-nitro-3-pyridinesulfonamide m.p. 46°–47° C.

N-Benzyl 6-benzylamino-5-nitro-3-pyridinesulfonamide m.p. 122°–123° C.

N-(p-Chlorobenzy) 6-(p-chlorobenzylamino)-5-nitro-3-pyridinesulfonamide m.p. 136°–138° C.

N-(p-Methoxybenzyl) 6-(p-methoxybenzylamino)-5-nitro-3-pyridinesulfonamide. m.p. 146°–148° C.

According to another aspect of this invention, novel compositions are provided in wich a pyridine derivative (I) is present as an active ingredient. Such compositons comprise the pyridine derivative intimately dispersed in or admixed with an inert carrier. The term "inert carrier" as used herein means are that is substantially nonreactive with the active ingredient, orally ingestable and tolerated by the poultry.

The amount of pyridine derivative required for control of coccidiosis in poultry will vary somewhat with the specific compound employed, the species of animals, the method or the object of application or with the symptoms. Generally, the pyridine derivatives (I) are effective in preventing the disease without undesirable side effect and toxic effect when administered at a level of more than about 0.004% by weight of the feed. For good prophylactic results, it is preferred that the feed contains between about 0.004 and 0.025% by weight of the active ingredient, more preferably between about 0.0075 and 0.0125%. When the pyridine derivatives are to be employed for therapeutic purpose, the higher levels are used for shorter period of time. Thus, the concentrations of about 0.05% to about 0.1% by weight of the feed may be advantageously administered for treatment of coccidiosis. When these compounds are to be employed for therapeutic purpose, it is desirable to employ the lowest levels that exhibit anticoccidial activities, in order to eliminate any risk of side effects that may appear on prolonged feeding.

In preparing solid compositions, a uniform dispersion of the active ingredient throughout the carrier can be readily accomplished by the conventional methods of grinding, stirring or milling.

Many of these pyridine derivatives are advantageously administered to poultry by way of the drinking water of the birds. This method of treatment may often be employed in the therapeutic use, since poultry with coccidiosis are apt to consume less solid feed than normal birds.

According to still another aspect of this invention, novel compositions are provided in which active ingredient is present in relatively large amounts and which are suitable for addition to the poultry feed directly or after intermediate dilution step. Such compositions which are a preferred feature of this invention are the so-called feed supplements or premix. Representative examples of the carriers to be employed in this invention are solid oral carriers such as distillers dried grains, corn starch, potato starch, fermentation residues, ground oyster shells, Attapulgus clay, rice bran, wheat bran, wheat middling, molasses solubles, corn meal, edible vegetable substances, soybean cake, soybean meal, antibiotic mycelis, crushed lime stone and the like.

Formulations containing from about 5% to about 30% by weight, and preferably from about 10 - 25% by weight, of the active ingredient are particularly suitable for this purpose. It is preferable in the industry to use about 1 - 3 kg. of such a supplement per ton of feed.

According to another aspect of this invention, the present composition may preferably include other known anticoccidial agents to broaden its anticoccidial spectrum and, sometimes, expect a synergistic effect.

Suitable examples of such anticoccidial agents include, for example, sulfa drugs, e.g., Sulfachloropyrazine, Sulfadimethoxine, Sulfaquinoxaline; thiamine derivatives, e.g., Beclotiamine, Amprolium, Dimethialium; quinoline derivatives, e.g., Buquinolate, Decoquinate, Methyl Benzoquate; folic acid antagonistic substances, e.g., pyrimethamin, Diaveridine; antibiotics, e.g., Monesin; Zolene (3,5-dinitro-o-toluamide), Clopidol (3,5-dichloro-2,6-dimethyl-4-pyridinol), Robenzidine; and the like.

The formulation of the compounds and the coccidiostatic activity of the compounds are more fully illustrated by the non-limiting examples as follows.

In these examples, all the parts are given by weight unless otherwise indicated.

The following are three typical formulations for feed supplements in accordance with the present invention:

| Formulation A | parts by weight |
|---|---|
| M-methyl 5-nitro-3-pyridinesulfonamide | 25 |
| wheat bran |  |
| Formulation B | parts by weight |
| 5-nitro-3-pyridine sulfonamide | 20 |
| rice bran | 80 |
| Formulation C | parts by weight |
| N-ethyl 6-amino-5-nitro-3-pyridinesulfonamide | 10 |
| soybean meal | 90 |
| Formulation D | parts by weight |
| N-methyl 6-methylamino-5-nitro-5-pyridinesulfonamide | 15 |
| wheat bran | 45 |
| soybean meal | 40 |

The coccidiostatic activity of the pyridine derivatives (I) of this invention is determined by the following method:

Test Procedures (1) Chicks: Fourteen-day-old White Leghorn males (after hatched, fed a diet containing no anticoccidial agent and isolated as far as possible from the risk of extraneous coccidial infections) were used.

Each group consisted of 10 chicks so as to avoid the difference of mean weight (significance level, 5%). (2) Infections: Each chick was inoculated orally into the crop with 42,000 sporulated oocysts of *Eimeria tenella*. (3) Concentration of tested compounds: Each tested compound as indicated below as mixed to the commercially available mixed feed at the concentration of 200 ppm. (4) Test procedures: The above chicks were isolated from those suffering coccidiosis and observed on their states of health. Normal healthy chicks were weighed and divided into groups, each consisting of 10 chicks so as to avoid the significant difference of average body weight (significance level 5%). On the other hand, two control groups of infected and non-medicated chicks and non-infected and non-medicated ones were separately prepared. After dividing into groups, a given number of oocysts were inoculated to all groups except for the non-infected and non-medicated control group, simultaneously with the feeding of a diet containing the test compound. Two control groups were fed with a diet which has the same formula (the same lot) and not test compound. (5) Evaluation: They are weighed from the beginning of the test to the end (when administered and infected) constantly. Daily oocysts outputs are determined as oocysts per gram feces during a period from day 4 to 6 after infection. The daily samples from each treatment are pooled and recorded as a percentage to that of the infected and non-medicated control. After 7 days from the infection, all chicks are sacrificed and the degree of the lesion of ceca are indicated as a 0 to 4 visual scale and determined by the method of Johnson and Reid described in Experimental Parasitology vol. 28, 30 - 36 pp., (1970).

Evaluation item's values are calculated according to the following equations, respectively.

(i) Rate of oocyst production (%)

$$\text{Rate of oocyst production (\%)} = \frac{\text{Oocyst outputs of each group}}{\text{Oocyst outputs of infected and non-medicated group}} \times 100 \quad \text{(i)}$$

The accumulated oocyst outputs per gram feces, on 6 or 7 days after infection, is defined as "oocyst number".

(ii) Relative rate of weight grain (%)

$$\text{Relative rate of weight grain (\%)} = \frac{\text{Average weight gain of each group}}{\text{Average weight gain of non-infected and non-medicated group}} \times 100 \quad \text{(ii)}$$

The total of the weight gain from the beginning of the test to the end divided with the number of the chicks is defined as "average weight gain".

(iii) Mean lesion score of cecum $$\text{Mean lesion score of cecum} = \frac{\text{Total cecum lesion of scores}}{\text{Number of chicks}} \quad \text{(iii)}$$

(iv) Mortality $$\text{Mortality} = \frac{\text{Number of chicks at the end of test}}{\text{Number of chicks at the beginning of test}} \times 100 \quad \text{(iv)}$$

The results are listed in the following Table.

Table

| Compound No. | Rate of oocyst production (%) | Relative rate of weight gain (%) | Mean lesion score of cecum | Mortality (%) |
|---|---|---|---|---|
| 1 | 0 | 97.6 | 0 | 0 |
| 2 | 0 | 98.5 | 0 | 0 |
| 9 | 0 | 98.0 | 0 | 0 |
| 17 | 0.4 | 90.0 | 0 | 0 |
| 19 | 0 | 96.8 | 0 | 0 |
| 27 | 0 | 97.4 | 0 | 0 |
| 34 | 0 | 92.3 | 0 | 0 |
| 37 | 5.2 | 89.5 | 1.2 | 0 |
| 53 | 0.1 | 95.5 | 0.1 | 0 |
| 62 | 0 | 98.0 | 0.1 | 0 |
| 70 | 0 | 98.9 | 0 | 0 |
| 71 | 7.5 | 89.9 | 1.6 | 0 |
| 73 | 0 | 99.8 | 0 | 0 |
| 85 | 5.7 | 90.4 | 0.7 | 0 |
| 94 | 0 | 91.6 | 0 | 0 |
| 102 | 0 | 92.0 | 0.1 | 0 |
| 111 | 0 | 92.0 | 0 | 0 |
| 112 | 0.7 | 90.1 | 0.2 | 0 |
| 119 | 0 | 91.5 | 0 | 0 |
| 135 | 2.5 | 89.8 | 0.8 | 0 |

| Compound No. | Rate of oocyst production (%) | Relative rate of weight gain (%) | Mean lesion score of cecum | Mortality (%) |
|---|---|---|---|---|
| Infected-non-medicated control | 100 | 50 | 4.0 | 20 |
| Uninfected-non-medicated control | 0 | 100 | 0 | 0 |

It will be evident from the above results that the pyridine derivatives of the abovementioned formula (I) possess an extremely high degree of an anticoccidial activity against acute coccidiosis caused by *E. tenella*, accompanying with good weight gain of the poultry without any unfavorable side effects.

What is claimed is:

1. A compound having the formula

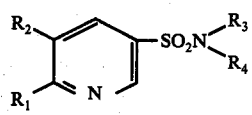

wherein
$R_1$ represents hydrogen atom, amino group or a group

in which $R_5$ and $R_6$ may be the same or different and each represents an alkyl group of 1 to 4 carbon atoms or $R_5$ is hydrogen atom and $R_6$ represents an alkyl group of 1 to 4 carbon atoms, an alkenyl group of 3 or 4 carbon atoms or a benzyl group optionally substituted with halogen, cyano, alkyl of 1 to 4 carbon atoms or alkoxy of 1 to 4 carbon atoms;

$R_2$ represents nitro group or an alkylamino group of 1 to 3 carbon atoms;

$R_3$ and $R_4$ individually represent hydrogen atom, an alkyl group of 1 to 4 carbon atoms, an alkoxyalkyl group which has 1 to 4 carbon atoms in the alkoxy moiety and 2 to 4 carbon atoms in the alkyl moiety, an alkenyl group of 3 or 4 carbon atoms, an alkanoyl group of 1 to 18 carbon atoms or a benzyl group optionally substituted with halogen, cyano, alkyl of 1 to 4 carbon atoms or alkoxy of 1 to 4 carbon atoms; provided that when $R_1$ is hydrogen atom and $R_2$ is nitro group, $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group, said alkenyl group, said alkanoyl group or said benzyl group, when $R_1$ is hydrogen atom and $R_2$ is said alkylamino group, $R_3$ and $R_4$ individually is hydrogen atom or they may be the same or different and each represents said alkyl group, when $R_1$ is amino group and $R_2$ is nitro group, $R_3$ and $R_4$ may be the same or different and each represents said alkyl group or $R_3$ is hydrogen atom and $R_4$ is said alkyl group or said alkenyl group, and when $R_1$ is said group

and $R_2$ is nitro group, $R_3$ and $R_4$ are the same as defined above with respect to the $R_5$ and $R_6$.

2. A compound according to claim 1 wherein $R_1$ is hydrogen atom and $R_2$ is nitro group, $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group, said alkenyl group, said alkanoyl group or said benzyl group.

3. A compound according to claim 1 wherein $R_1$ is hydrogen atom and $R_2$ is said alkylamino group, $R_3$ and $R_4$ individually is hydrogen atom or they may be the same or different and each represents said alkyl group.

4. A compound according to claim 1 wherein $R_1$ is amino group and $R_2$ is nitro group, $R_3$ and $R_4$ may be the same or different and each represents said alkyl group or $R_3$ is hydrogen atom and $R_4$ is said alkyl group or said alkenyl group.

5. A compound according to claim 1 wherein $R_1$ is said group

and $R_2$ is nitro group, $R_3$ and $R_4$ are the same as defined above with respect to the $R_5$ and $R_6$.

6. A compound according to claim 1 wherein $R_1$ is hydrogen atom, $R_2$ is nitro group, and $R_3$ and $R_4$ may be the same or differet and each represents said alkyl group or said alkoxyalkyl group or $R_3$ is hydrogen atom and $R_4$ is hydrogen atom, said alkyl group, said alkoxyalkyl group or an alkanoyl group of 2 to 8 carbon atoms.

7. A compound according to claim 1 wherein $R_1$ is hydrogen atom, and $R_3$ and $R_4$ may be the same or different and each represents methyl group or ethyl group.

8. A compound according to claim 1 wherein $R_1$ is amino group, $R_2$ is nitro group and $R_3$ and $R_4$ may be the same or different and each represents methyl group or ethyl group or $R_3$ is hydrogen atom and $R_4$ is methyl group or ethyl group.

9. A compound according to claim 1 wherein $R_1$ is the group

in which $R_5$ and $R_6$ may be the same or different and each represents methyl group or ethyl group or $R_5$ is hydrogen atom and $R_6$ is methyl group or ethyl group, $R_2$ is nitro group, $R_3$ and $R_4$ are as defined above with respect to the above $R_5$ and $R_6$.

10. A compound according to claim 1 wherein $R_1$ is hydrogen atom, $R_2$ is nitro group and $R_3$ and $R_4$ may be the same or different and each represents said alkyl group or said alkoxyalkyl group or $R_3$ is hydrogen atom and $R_4$ is hydrogen atom, said alkyl group or said alkoxyalkyl group; wherein $R_1$ is amino group, $R_2$ is nitro group and $R_3$ and $R_4$ may be the same or different and each represents methyl group or ethyl group or $R_3$ is hydrogen atom and $R_4$ is methyl group or ethyl group; or wherein $R_1$ is dimethylamino group or methylamino group, $R_2$ is nitro group and $R_3$ and $R_4$ individually represent methyl group or $R_3$ is hydrogen atom and $R_4$ is methyl group.

11. A compound according to claim 1 wherein $R_1$ is hydrogen atom, $R_2$ is nitro group and $R_3$ and $R_4$ may be the same or different and each represents said alkyl group or said alkoxyalkyl group or $R_3$ is hydrogen atom and $R_4$ is hydrogen atom, said alkyl group or said alkoxyalkyl group; or wherein $R_1$ is dimethylamino group or methylamino group, $R_2$ is nitro group and $R_3$ and $R_4$ individually represent methyl group or $R_3$ is hydrogen atom and $R_4$ is methyl group.

12. N-Methyl 5-nitro-3-pyridinesulfonamide.
13. N-Ethyl 5-nitro-3-pyridinesulfonamide.
14. N-n-Propyl 5-nitro-3-pyridinesulfonamide.
15. N,N-Dimethyl 5-nitro-3-pyridinesulfonamide.
16. N-n-Butyl-N-ethyl 5-nitro-3-pyridinesulfonamide.
17. N-(2-Ethoxyethyl) 5-nitro-3-pyridinesulfonamide.
18. N-(3-Isopropoxypropyl) 5-nitro-3-pyridinesulfonamide.
19. N-(2-Ethoxyethyl)-N-ethyl 5-nitro-3-pyridinesulfonamide.
20. N-Benzyl 5-nitro-3-pyridinesulfonamide.
21. N-Acetyl 5-nitro-3-pyridinesulfonamide.
22. N-Octanoyl 5-nitro-3-pyridinesulfonamide.
23. 5-Nitro-3-pyridinesulfonamide.
24. N,N-Diethyl 5-ethylamino-3-pyridinesulfonamide.
25. N-Methyl 6-amino-5-nitro-3-pyridinesulfonamide.
26. N-Ethyl 6-amino-5-nitro-3-pyridinesulfonamide.
27. N,N-Dimethyl 6-amino-5-nitro-3-pyridinesulfonamide.
28. N,N-Diethyl 6-amino-5-nitro-3-pyridinesulfonamide.
29. N-Methyl 6-methylamino-5-nitro-3-pyridinesulfonamide.
30. N-Ethyl 6-ethylamino-5-nitro-3-pyridinesulfonamide.
31. N-n-Butyl 6-n-butylamino-5-nitro-3-pyridinesulfonamide.
32. N,N-Dimethyl 6-dimethylamino-5-nitro-3-pyridinesulfonamide.
33. N,N-Diethyl 6-diethylamino-5-nitro-3-pyridinesulfonamide.
34. N-Benzyl 6-benzylamino-5-nitro-3-pyridinesulfonamide.
35. N-(p-Chlorobenzyl) 6-(p-chlorobenzylamino)-5-nitro-3-pyridinesulfonamide.
36. N-(p-Methoxybenzyl) 6-(p-methoxybenzylamino)-5-nitro-3-pyridinesulfonamide.

37. An anticoccidal composition containing an amount, sufficient to inhibit coccidiosis, of a compound having the formula

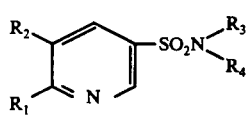

intimately mixed with an inert carrier, wherein
$R_1$ represents hydrogen atom, amino group or a group

in which $R_5$ and $R_6$ may be the same or different and each represents an alkyl group of 1 to 4 carbon atoms or $R_5$ is hydrogen atom and $R_6$ represents an alkyl group of 1 to 4 carbon atoms, an alkenyl group of 3 or 4 carbon atoms or a benzyl group optionally substituted with halogen, cyano, alkyl of 1 to 4 carbon atoms or alkoxy of 1 to 4 carbon atoms;

$R_2$ represents nitro group or an alkylamino group of 1 to 3 carbon atoms;

$R_3$ and $R_4$ individually represent hydrogen atom, an alkyl group of 1 to 4 carbon atoms, an alkoxyalkyl group which has 1 to 4 carbon atoms in the alkoxy moiety and 2 to 4 carbon atoms in the alkyl moiety, an alkenyl group of 3 or 4 carbon atoms, an alkanoyl group of 1 to 18 carbon atoms or a benzyl group optionally substituted with halogen, cyano, alkyl of 1 to 4 carbon atoms or alkoxy of 1 to 4 carbon atoms; provided that when $R_1$ is hydrogen atom and $R_2$ is nitro group, $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group, said alkenyl group, said alkanoyl group or said benzyl group, when $R_1$ is hydrogen atom and $R_2$ is said alkylamino group, $R_3$ and $R_4$ individually is hydrogen atom or they may be the same or different and each represents said alkyl group, when $R_1$ is amino group and $R_2$ is nitro group, $R_3$ and $R_4$ may be the same or different and each represents said alkyl group or $R_3$ is hydrogen atom and $R_4$ is said alkyl group or said alkenyl group, and when $R_1$ is said group

and $R_2$ is nitro group, $R_3$ and $R_4$ are the same as defined above with respect to the $R_5$ and $R_6$.

38. A composition according to claim 37 wherein $R_1$ is hydrogen atom and $R_2$ is nitro group, $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group, said alkenyl group, said alkanoyl group or said benzyl group.

39. A composition according to claim 37 wherein $R_1$ is hydrogen atom and $R_2$ is said alkylamino group, $R_3$ and $R_4$ individually is hydrogen atom or they may be the same or different and each represents said alkyl group.

40. A composition according to claim 37 wherein $R_1$ is amino group and $R_2$ is nitro group, $R_3$ and $R_4$ may be the same or different and each represents said alkyl group, or $R_3$ is hydrogen atom and $R_4$ is said alkyl group or said alkenyl group.

41. A composition according to claim 37 wherein $R_1$ is said group

and $R_2$ is nitro group, $R_3$ and $R_4$ are the same as defined above with respect to the $R_5$ and $R_6$.

42. A composition according to claim 37 wherein $R_1$ is hydrogen atom, $R_2$ is nitro group, and $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group or an alkanoyl group of 2 to 8 carbon atoms.

43. A composition according to claim 37 wherein $R_1$ is hydrogen atom, and $R_3$ and $R_4$ may be the same or different and each represents methyl group or ethyl group.

44. A composition according to claim 37 wherein $R_1$ is amino group, $R_2$ is nitro group and $R_3$ and $R_4$ may be the same or different and each represents methyl group or ethyl group or $R_3$ is hydrogen atom and $R_4$ is methyl group or ethyl group.

45. A composition according to claim 37 wherein $R_1$ is the group

in which $R_5$ and $R_6$ may be the same or different and each represents methyl group or ethyl group or $R_5$ is hydrogen atom and $R_6$ is methyl group or ethyl group, $R_2$ is nitro group, $R_3$ and $R_4$ are as defined above with respect to the above $R_5$ and $R_6$.

46. A composition according to claim 37 wherein $R_1$ is hydrogen atom, $R_2$ is nitro group and $R_3$ and $R_4$ may be the same or different and each represents said alkyl group or said alkoxyalkyl group or $R_3$ is hydrogen atom and $R_4$ is hydrogen atom, said alkyl group or said alkoxyalkyl group; wherein $R_1$ is amino group, $R_2$ is nitro group and $R_3$ and $R_4$ may be the same or different and each represents methyl group of ethyl group or $R_3$ is hydrogen atom and $R_4$ is methyl group or ethyl group; or wherein $R_1$ is dimethylamino group or methylamino group, $R_2$ is nitro group and $R_3$ and $R_4$ individually represent methyl group or $R_3$ is hydrogen atom and $R_4$ is methyl group.

47. A composition according to claim 37 wherein $R_1$ is hydrogen atom, $R_2$ is nitro group and $R_3$ and $R_4$ may be the same or different and each represents said alkyl group or said alkoxyalkyl or $R_3$ is hydrogen atom and $R_4$ is hydrogen atom, said alkyl group or said alkoxyalkyl group; or wherein $R_1$ is dimethylamino group or methylamino group, $R_2$ is nitro group and $R_3$ and $R_4$ individually represent methyl group or $R_3$ is hydrogen atom and $R_4$ is methyl group.

48. A composition according to claim 37 wherein said compound is selected from the group consisting of
N-Methyl 5-nitro-3-pyridinesulfonamide,
N-Ethyl 5-nitro-3-pyridinesulfonamide,
N-n-Propyl 5-nitro-3-pyridinesulfonamide,
N,N-Dimethyl 5-nitro-3-pyridinesulfonamide,
N-n-Butyl-N-ethyl 5-nitro-3-pyridinesulfonamide,
N-(2-ethoxyethyl) 5-nitro-3-pyridinesulfonamide,
N-(3-Isopropoxypropyl) 5-nitro-3-pyridinesulfonamide,
N-(2-Ethoxyethyl)-N-ethyl 5-nitro-3-pyridinesulfonamide,
N-Benzyl 5-nitro-3-pyridinesulfonamide,
N-Acetyl 5-nitro-3-pyridinesulfonamide,
N-Octanoyl 5-nitro-3-pyridinesulfonamide,
5-Nitro-3-pyridinesulfonamide,
5-Amino-3-pyridinesulfonamide,
N,N-Diethyl 5-ethylamino-3-pyridinesulfonamide,
N-Methyl 6-amino-5-nitro-3-pyridinesulfonamide,
N-Ethyl 6-amino-5-nitro-3-pyridinesulfonamide,
N,N-Dimethyl 6-amino-5-nitro-3-pyridinesulfonamide,
N,N-Diethyl 6-amino-5-nitro-3-pyridinesulfonamide,
N-Methyl 6-methylamino-5-nitro-3-pyridinesulfonamide,
N-Ethyl 6-ethylamino-5-nitro-3-pyridinesulfonamide,
N-n-Butyl 6-n-butylamino-5-nitro-3-pyridinesulfonamide,
N,N-Dimethyl 6-dimethylamino-5-nitro-3-pyridinesulfonamide,
N,N-Diethyl 6-diethylamino-5-nitro-3-pyridinesulfonamide,
N-Benzyl 6-benzylamino-5-nitro-3-pyridinesulfonamide,
N-(p-Chlorobenzyl) 6(p-chlorobenzylamino)-5-nitro-3-pyridinesulfonamide and
N-(p-Methoxybenzyl) 6-(p-methoxybenzylamino)-5-nitro-3-pyridinesulfonamide.

49. A poultry feed having dispersed therein for control of poultry coccidiosis at least 0.005% by weight of a compound having the formula

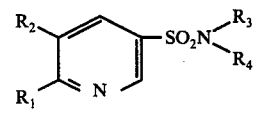

wherein
$R_1$ represents hydrogen atom, amino group or a group

in which $R_5$ and $R_6$ may be the same or different and each represents an alkyl group of 1 to 4 carbon atoms or $R_5$ is hydrogen atom and $R_6$ represents an alkyl group of 1 to 4 carbon atoms, an alkenyl group of 3 or 4 carbon atoms or a benzyl group optionally substituted with halogen, cyano, alkyl of 1 to 4 carbon atoms or alkoxy of 1 to 4 carbon atoms;
$R_2$ represents nitro group or an alkylamino group of 1 to 3 carbon atoms;
$R_3$ and $R_4$ individually represent hydrogen atom, an alkyl group of 1 to 4 carbon atoms, an alkoxyalkyl group which has 1 to 4 carbon atoms in the alkoxy moiety and 2 to 4 carbon atoms in the alkyl moiety, an alkenyl group of 3 or 4 carbon atoms, an alkanoyl group of 1 to 18 carbon atoms or a benzyl group optionally substituted with halogen, cyano, alkyl of 1 to 4 carbon atoms or alkoxy of 1 to 4 carbon atoms; provided that when $R_1$ is hydrogen atom and $R_2$ is nitro group, $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group, said alkenyl group, said alkanoyl group or said benzyl group, when $R_1$ is hydrogen atom and $R_2$ is said alkylamino group, $R_3$ and $R_4$ individually is hydrogen atom or they may be the same or different and each represents said alkyl group, when $R_1$ is amino group and $R_2$ is nitro group, $R_3$ and $R_4$ may be the same or different and each represents said alkyl group or $R_3$ is hydrogen atom and $R_4$ is said alkyl group or said alkenyl group, and when $R_1$ is said group

and $R_2$ is nitro group, $R_3$ and $R_4$ are the same as defined above with respect to the $R_5$ and $R_6$.

50. A feed according to claim 49 wherein $R_1$ is hydrogen atom and $R_2$ is nitro group, $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group, said alkenyl group, said alkanoyl group or said benzyl group.

51. A feed according to claim 49 wherein $R_1$ is hydrogen atom and $R_2$ is said alkylamino group, $R_3$ and $R_4$ individually is hydrogen atom or they may be the same or different and each represents said alkyl group.

52. A feed according to claim 49 wherein $R_1$ is amino group and $R_2$ is nitro group, $R_3$ and $R_4$ may be the same or different and each represents said alkyl group or $R_3$ is hydrogen atom and $R_4$ is said alkyl group or said alkenyl group.

53. A feed according to claim 49 wherein $R_1$ is said group

and $R_2$ is nitro group, $R_3$ and $R_4$ are the same as defined above with respect to the $R_5$ and $R_6$.

54. A feed according to claim 49 wherein $R_1$ is hydrogen atom, $R_2$ is nitro group, and $R_3$ and $R_4$ may be the same or different and each represents said alkyl group or said alkoxyalkyl group or $R_3$ is hydrogen atom and $R_4$ is hydrogen atom, said alkyl group, said alkoxyalkyl group or an alkanoyl group of 2 to 8 carbon atoms.

55. A feed according to claim 49 wherein $R_1$ is hydrogen atom, and $R_3$ and $R_4$ may be the same or different and each represents methyl group or ethyl group.

56. A feed according to claim 49 wherein $R_1$ is amino group, $R_2$ is nitro group and $R_3$ and $R_4$ may be the same or different and each represents methyl group or ethyl group or $R_3$ is hydrogen atom and $R_4$ is methyl group or ethyl group.

57. A feed according to claim 49 wherein $R_1$ is the group

in which $R_5$ and $R_6$ may be the same or different and each represents methyl group or ethyl group or $R_5$ is hydrogen atom and $R_6$ is methyl group or ethyl group, $R_2$ is nitro group, $R_3$ and $R_4$ are as defined above with respect to the above $R_5$ and $R_6$.

58. A feed according to claim 49 wherein $R_1$ is hydrogen atom, $R_2$ is nitro group and $R_3$ and $R_4$ may be the same or different and each represents said alkyl group or said alkoxyalkyl group or $R_3$ is hydrogen atom and $R_4$ is hydrogen atom, said alkyl group or said alkoxyalkyl group; wherein $R_1$ is amino group, $R_2$ is nitro group and $R_3$ and $R_4$ may be the same or different and each represents methyl group or ethyl group or $R_3$ is hydrogen atom and $R_4$ is methyl group or ethyl group; or wherein $R_1$ is dimethylamino group or methylamino group, $R_2$ is nitro group and $R_3$ and $R_4$ individually represent methyl group or $R_3$ is hydrogen atom and $R_4$ is methyl group.

59. A feed according to claim 49 wherein $R_1$ is hydrogen atom, $R_2$ is nitro group and $R_3$ and $R_4$ may be the same or different and each represents said alkyl group or said alkoxyalkyl group or $R_3$ is hydrogen atom and $R_4$ is hydrogen atom, said alkyl group or said alkoxyalkyl group; or wherein $R_1$ is dimethylamino group or methylamino group, $R_2$ is nitro group and $R_3$ and $R_4$ individually represent methyl group or $R_3$ is hydrogen atom and $R_4$ is methyl group.

60. A feed according to claim 49 wherein said compound is selected from the group consisting of
N-Methyl 5-nitro-3-pyridinesulfonamide,
N-Ethyl 5-nitro-3-pyridinesulfonamide,
N-n-Propyl 5-nitro-3-pyridinesulfonamide,
N,N-Dimethyl 5-nitro-3-pyridinesulfonamide,
N-n-Butyl-N-ethyl 5-nitro-3-pyridinesulfonamide,
N-(2-Ethoxyethyl) 5-nitro-3-pyridinesulfonamide,
N-(3-Isopropoxypropyl) 5-nitro-3-pyridinesulfonamide,
N-(2-Ethoxyethyl)-N-ethyl 5-nitro-3-pyridinesulfonamide,
N-Benzyl 5-nitro-3-pyridinesulfonamide,
N-Acetyl 5-nitro-3-pyridinesulfonamide,
N-Octanoyl 5-nitro-3-pyridinesulfonamide,
5-Nitro-3-pyridinesulfonamide,
5-Amino-3-pyridinesulfonamide,
N,N-Diethyl 5-ethylamino-3-pyridinesulfonamide,
N-Methyl 6-amino-5-nitro-3-pyridinesulfonamide,
N-Ethyl 6-amino-5-nitro-3-pyridinesulfonamide,
N,N-Dimethyl 6-amino-5-nitro-3-pyridinesulfonamide,
N,N-Diethyl 6-amino-5-nitro-3-pyridinesulfonamide,
N-Methyl 6-methylamino-5-nitro-3-pyridinesulfonamide,
N-Ethyl 6-ethylamino-5-nitro-3-pyridinesulfonamide,
N-n-Butyl 6-n-butylamino-5-nitro-3-pyridinesulfonamide,
N,N-Dimethyl 6-dimethylamino-5-nitro-3-pyridinesulfonamide,
N,N-Diethyl 6-diethylamino-5-nitro-3-pyridinesulfonamide,
N-Benzyl 6-benzylamino-5-nitro-3-pyridinesulfonamide,
N-(p-Chlorobenzyl) 6-(p-chlorobenzylamino)-5-nitro-3-pyridinesulfonamide and
N-(p-Methoxybenzyl) 6-(p-methoxybenzylamino)-5-nitro-3-pyridinesulfonamide.

* * * * *

UNITED STATES PATENT AND TRADEMARK OFFICE
CERTIFICATE OF CORRECTION

PATENT NO. : 4,094,982
DATED : June 13, 1978
INVENTOR(S) : YASUHIRO MORISAWA et al It is certified that error appears in the above-identified patent and that said Letters Patent are hereby corrected as shown below:

12) Column 6, Compound 122: rewrite "N,N-di-isopropylamino..." as ---N,N-di-isopropyl 6-di-isopropylamino...---.

13) Column 6, Compound 131: rewrite "N-(m-methylbenzylamino)-" as ---N-(m-methylbenzyl) 6-(m-methylbenzylamino)- ---.

14) Column 6, after Compound 131: insert the following ---132. N-(p-methylbenzyl) 6-(p-methylbenzylamino)-5-nitro-3-pyridinesulfonamide---.

15) Column 6, Compound 133: rewrite "N-(o-methylbenzyl)" as ---N-(o-methoxybenzyl)---.

16) Column 6, Compound 134: after "...amino)-", insert ---5-nitro-3-pyridinesulfonamide---.

17) Column 7, line 19: after "an", insert ---acid---.

18) Column 10, line 57: after "1", insert ---hour---.

19) Column 11, line 13: after "Process III", insert ---:---, and after "atom", insert ---$R_2$ is amino group or said alkylamino group and---.

20) Column 12, line 13: after "The", rewrite "precipitated" as ---precipitate---.

21) Column 13, line 5: rewrite "produce" as ---product---.

UNITED STATES PATENT AND TRADEMARK OFFICE
CERTIFICATE OF CORRECTION

PATENT NO. : 4,094,982
DATED : June 13, 1978
INVENTOR(S) : YASUHIRO MORISAWA et al It is certified that error appears in the above-identified patent and that said Letters Patent are hereby corrected as shown below:

1) Column 2, line 2: rewrite "Sporozoa", "Coccidia" and "Eimeriidae" in italics.

2) Column 2, lines 4-5: rewrite "Eimeria" in italics.

3) Column 2, line 21: rewrite "Eimeria" in italics.

4) Column 3, line 27: delete "methyl-"; line 28: delete "benzyl,".

5) Column 5, Compound 23: rewrite "N-(2-methoxyropyl" as ---N-(2-methoxypropyl)---.

6) Column 5, Compound 39: replace "N-(m-chloroenzyl)" with ---N-(m-chlorobenzyl)---.

7) Column 5, Compound 40: replace "N-(p-chloroenzyl)" with ---N-(p-chlorobenzyl)---.

8) Column 5, Compound 46: before "-nitro", insert ---5---.

9) Column 5, Compound 69: rewrite "N-stearoyll" as ---N-stearoyl---.

10) Column 5, Compound 87: rewrite "N,N-di-inopropyl" as ---N,N-di-isopropyl---.

11) Column 6, Compound 117: rewrite "6-n-butylamino..." as ---6-sec-butylamino...---.

UNITED STATES PATENT AND TRADEMARK OFFICE
CERTIFICATE OF CORRECTION

PATENT NO. : 4,094,982

DATED : June 13, 1978

INVENTOR(S) : YASUHIRO MORISAWA et al

It is certified that error appears in the above–identified patent and that said Letters Patent are hereby corrected as shown below:

22) Column 14, line 11: "N-(p-Chlorobenzy)" should be ---N-(p-Chlorobenzyl)---.

23) Column 14, line 16: rewrite "wich" as ---which---.

24) Column 14, line 20: after "means", replace "are" with ---one---.

25) Column 15, line 17: rewrite "Monesin" as ---Monensin---.

26) Column 15, line 30: under "25", add ---75---.

27) Column 15, line 56: after "below", replace "as" with --was--.

28) Column 15, line 67: replace "were" with ---was---.

29) Column 20, line 55 (Claim 40): delete the comma before "or".

30) Column 21, line 32 (Claim 46): before "ethyl", replace "of" with ---or---.

Signed and Sealed this

Twenty-third Day of October 1979

[SEAL]

Attest:

RUTH C. MASON
Attesting Officer

LUTRELLE F. PARKER
Acting Commissioner of Patents and Trademarks